(12) United States Patent  
Tenaglia

(10) Patent No.: US 7,861,573 B1  
(45) Date of Patent: Jan. 4, 2011

(54) LASER SHOCK INDUCED SPALLATION

(75) Inventor: Richard D. Tenaglia, Westerville, OH (US)

(73) Assignee: LSP Technologies, Inc., Dublin, OH (US)

( * ) Notice: Subject to any disclaimer, the term of this patent is extended or adjusted under 35 U.S.C. 154(b) by 230 days.

(21) Appl. No.: 11/946,139

(22) Filed: Nov. 28, 2007

(51) Int. Cl.  
*G01M 7/00* (2006.01)

(52) U.S. Cl. ..................................... 73/12.08

(58) Field of Classification Search ...... 73/12.01–12.14  
See application file for complete search history.

(56) References Cited

U.S. PATENT DOCUMENTS

| | | | | |
|---|---|---|---|---|
| 5,438,402 A | * | 8/1995 | Gupta | 356/35.5 |
| 5,838,446 A | * | 11/1998 | Meth et al. | 356/632 |
| 5,916,811 A | * | 6/1999 | Stroosnijder et al. | 436/5 |
| 6,539,773 B2 | * | 4/2003 | Clauer et al. | 73/11.02 |
| 6,747,240 B2 | * | 6/2004 | Tenaglia et al. | 219/121.6 |
| 6,796,709 B2 | * | 9/2004 | Choi | 374/102 |
| 7,268,317 B2 | * | 9/2007 | Tenaglia et al. | 219/121.85 |
| 2003/0015508 A1 | * | 1/2003 | Tenaglia et al. | 219/121.69 |
| 2004/0011774 A1 | * | 1/2004 | Tenaglia et al. | 219/121.85 |

* cited by examiner

*Primary Examiner*—Max Noori  
(74) *Attorney, Agent, or Firm*—Benjamen E. Kern

(57) ABSTRACT

Laser shock methods and systems are disclosed for evaluating impact resistance of materials, and for simulating and evaluating threshold conditions where damage may occur.

22 Claims, 17 Drawing Sheets

From right to left – spots 1,2, and 3; 7.5J, 20 ns, 1.9 GW/cm$^2$

From right to left – spots 4,5, and 6; 5J, 20 ns, 1.3 GW/cm$^2$

From right to left – spot 7 (34J, 20 ns, 8.5 GW/cm$^2$), spots 8 and 9 (20J, 20 ns, 5.1 GW/cm$^2$)

From right to left - spots 1, 2, and 3; 35 J, 20 ns, 8.9 GW/cm$^2$

From right to left - spots 4, 5, and 6; 20 J, 20 ns, 5.1 GW/cm$^2$

From right to left - spots 7, 8, and 9; 10 J, 20 ns, 2.6 GW/cm$^2$

US 7,861,573 B1

LASER SHOCK INDUCED SPALLATION

This invention was made with United States Government support under Army Contract No. W911QX-04-P-0241, awarded by the United States Army Research Laboratory. The United States Government has certain rights in the invention.

BACKGROUND

Ceramic tiles may be used by military and law enforcement personnel. For example, ceramic tiles may be placed into clothing worn by soldiers and police officers as personal body armor to protect against small arms fire and explosion fragments. Ceramic tile may also be use as armor plating on personnel carriers and fighting vehicles, such as tanks. Various engineering ceramics, such as silicon carbide, boron carbide, alumina, zirconia, and the like have been used for this purpose. The high hardness of these materials has been shown to be effective for preventing penetration of kinetic energy penetrators (i.e., projectiles).

Tiles of engineering glass, such as borosilicate glass and soda lime glass, are similarly used to resist chemical energy penetrators, where the projectile weapon creates a plasma jet designed to burn through the armor on armored vehicles.

Routine testing of ceramic and glass tiles during development and production has proven challenging. Traditional methods of testing, such as ballistics testing, require precise alignment of the projectile path with the tile surface, which can be tedious, time consuming, and costly, and may hinder reproducibility. In addition, ballistics testing lacks sufficient sensitivity to identify the threshold energy for damage, or to distinguish between various production parameters used to manufacture the tiles. Conventional ballistic testing of ceramic armor is described in *Aspects of Geometry Affecting the Ballistic Performance of Ceramic Targets*, I. M. Pickup, et al., Ceramic Transactions, Vol, 134, pp, 643-50 (2002).

SUMMARY

In one embodiment, a method of evaluating impact resistance of a ceramic material is provided, comprising: applying an energy absorbing overlay to a portion of a front surface of the ceramic material; applying a substantially transparent overlay upon the energy absorbing overlay; directing a pulse of coherent energy to the energy absorbing overlay, generating at least one shockwave for transmission to the ceramic material; and detecting spallation on a back surface of the ceramic material.

In another embodiment, a method of evaluating impact resistance of a glass material is provided, comprising: applying an energy absorbing overlay to a portion of a front surface of the glass material; applying a substantially transparent overlay upon the energy absorbing overlay; directing a pulse of coherent energy to the energy absorbing overlay, generating at least one shockwave for transmission to the glass material; and detecting damage within the glass material.

In yet another embodiment, a method of identifying a threshold energy for damage to an article is provided, comprising: exposing a surface of the article to a laser pulse having an intensity, thereby generating at least one first shockwave into the article; detecting spallation on an opposing surface of the article as a result of the first shockwave generation; modifying at least one laser pulse parameter to increase the intensity of the laser pulse; exposing the surface of the article to a laser pulse having the modified laser pulse parameter, generating at least one second shockwave; and detecting spallation on the opposing surface of the article.

In another embodiment, a method of testing the adhesion of a coating on a coated material is provided, the method comprising: applying an energy absorbing overlay to a portion of a front surface of the coated material; applying a substantially transparent layer upon the energy absorbing overlay; exposing the energy absorbing overlay to a laser pulse, generating at least one shockwave for transmission to the coated material; and detecting spallation on a back surface of the coated material.

In another embodiment, a system for evaluating impact resistance of an article is provided, the system comprising: a laser source configured to expose a front surface of the article to a laser beam capable of imparting a shockwave to the article; an applicator' configured to apply a substantially opaque overlay to the front surface; an applicator configured to apply a substantially transparent overlay upon the substantially opaque overlay; and a detector configured to detect damage in at least one of a back surface of the article and within the article.

BRIEF DESCRIPTION OF THE DRAWINGS

The accompanying figures, which are incorporated in and constitute a part of the specification, illustrate various example systems, methods, results, and so on, and are used merely to illustrate various example embodiments. It should be noted that various components depicted in the figures may not be drawn to scale. The exemplary results presented in the figures are presented for purposes of illustration only, and should not be considered in any way as limiting.

DETAILED DESCRIPTION

Figure 1:
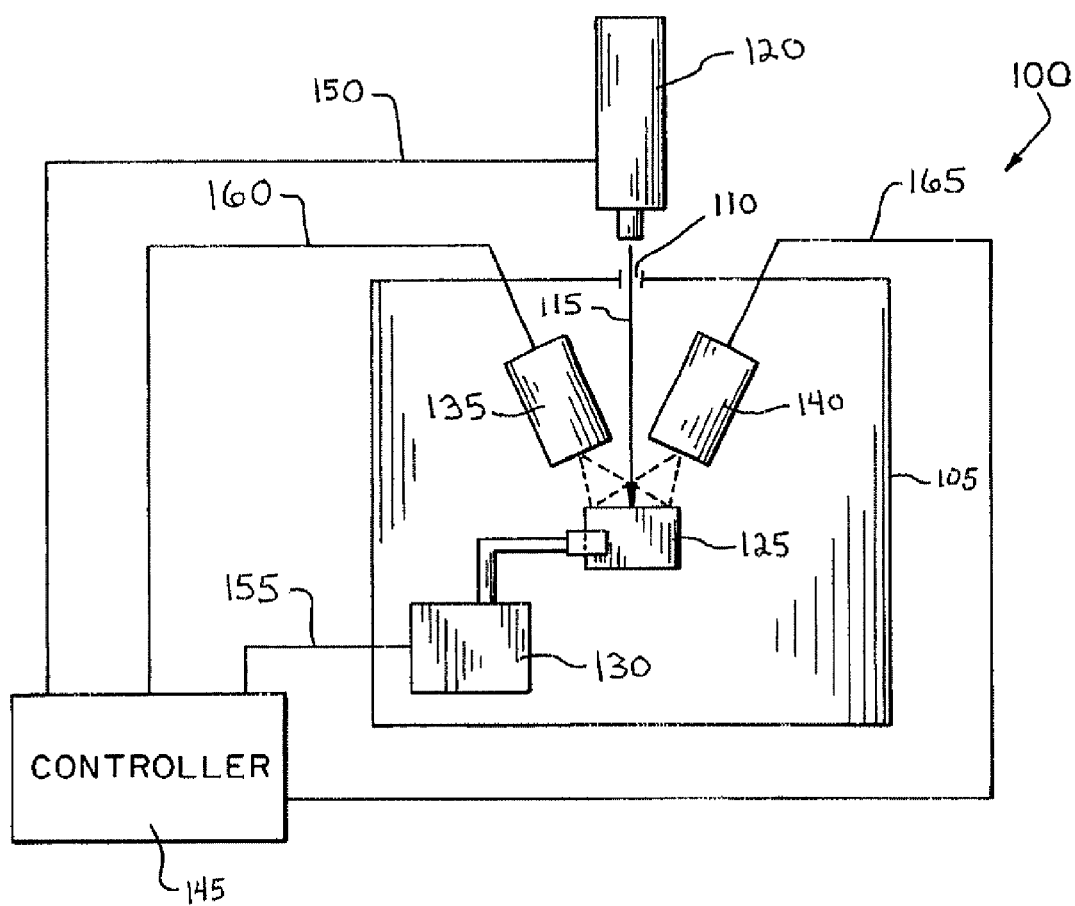
FIG. 1 illustrates an exemplary system for evaluating impact resistance of an article.

In one embodiment, a method of evaluating impact resistance of a ceramic material is provided, comprising: applying an energy absorbing overlay to a portion of a front surface of the ceramic material; applying a substantially transparent overlay upon the energy absorbing overlay; directing a pulse of coherent energy to the energy absorbing overlay, generating at least one shockwave for transmission to the ceramic material; and detecting spallation on a back surface of the ceramic material.

In one embodiment, the detecting comprises detecting visually. The method may further comprise detecting damage within the ceramic tile. For example, the detecting damage may comprise detecting damage ultrasonically. The method may further comprise measuring at least one of a diameter and a depth of the spallation. The method may further comprise correlating at least one of the diameter and depth of the spallation to at least one laser pulse parameter. In one embodiment, the laser pulse parameter may be selected from at least one of a laser spot diameter, a laser beam energy, a temporal pulse duration, and a laser fluence. The ceramic material may be selected from a variety of materials, including but not limited to, silicon carbide, boron carbide, alumina, zirconia, and mixtures thereof.

In one embodiment, a method of evaluating impact resistance of a glass material is provided, the method comprising: applying an energy absorbing overlay to a portion of a front surface of the glass material; applying a substantially transparent overlay upon the energy absorbing overlay; directing a pulse of coherent energy to the energy absorbing overlay, generating at least one shockwave for transmission to the glass material; and detecting damage within the glass material.

In one exemplary embodiment, the detecting may comprise detecting visually or ultrasonically. The method may further comprise detecting a diameter of damage and a depth of damage. The method may further comprise correlating at least one of the diameter of damage and depth of the damage to at least one laser pulse parameter. The glass material may be selected from borosilicate glass and soda lime glass, among others.

In another embodiment, a method of identifying a threshold energy for damage to an article is provided, the method comprising: exposing a surface of the article to a laser pulse having an intensity, thereby generating at least one first shockwave into the article; detecting spallation on an opposing surface of the article as a result of the first shockwave generation; modifying at least one laser pulse parameter to increase the intensity of the laser pulse; exposing the surface of the article to a laser pulse having the modified laser pulse parameter, generating at least one second shockwave; and detecting spallation on the opposing surface of the article.

The method may further comprise correlating the intensity of the laser pulse to a depth or a diameter of the spallation to determine the threshold energy for damage to the article. The method may further comprise correlating the modified laser pulse parameter to a depth or a diameter of the spallation to determine the threshold energy for damage to the article. In one embodiment, the laser pulse parameter may be selected from a laser spot diameter, a laser beam energy, a temporal pulse duration, and a laser fluence.

In yet another embodiment, a method of testing the adhesion and/or the integrity of a coating on a coated material is provided, the method comprising: applying an energy absorbing overlay to a portion of a front surface of the coated material; applying a substantially transparent overlay upon the energy absorbing overlay; exposing the energy absorbing overlay to a laser pulse, generating at least one shockwave for transmission to the coated material; and detecting spallation on a back surface of the coated material. In one embodiment of the method, the coating comprises at least one of a flame coating, a plasma coating, a paint coating, and an oxide coating.

In still another embodiment, a system for evaluating impact resistance of an article is provided, the system comprising: a laser source configured to expose a front surface of the article to a laser beam capable of imparting a shockwave to the article; an applicator configured to apply a substantially opaque overlay to the front surface; an applicator configured to apply a substantially transparent overlay upon the substantially opaque overlay; and a detector configured to detect damage in at least one of a back surface of the article and within the article.

FIG. 1 illustrates an exemplary system for evaluating impact resistance of an article. Thus, laser shock system 100 may include a target chamber 105 in which the laser shock process takes place. The target chamber 105 includes an opening 110 for a laser beam 115 created by laser 120, a source of coherent energy. Laser 120, by way of example, may be a commercially available high power pulse laser system. Typical laser shocking apparatuses, devices, and systems include, for example, those disclosed in U.S. Pat. No. 5,131,957 and U.S. Pat. No. 5,741,559, both of which are incorporated herein by reference in their entirety, and the like. Other types of exemplary lasers adaptable for use with the present embodiments include Nd-glass lasers manufactured by LSP Technologies, Inc. of Dublin, Ohio. The laser pulse length and focus of the laser beam may be adjusted as known in the art.

As shown in FIG. 1, a target material 125 is held in position within target chamber 105 by a positioning mechanism 130. Positioning mechanism 130 may be a robotically controlled arm or other apparatus to precisely position target material 125 relative to the operational elements of laser shock system 100. System 100 may include a material applicator 135 for applying an energy absorbing material onto target material 125 to create a coated portion. Material applicator 135 may be a solenoid operated painting station or other construction such as a jet spray or aerosol unit to provide a small coated area onto target material 125. The energy absorbing material may be substantially opaque and may include, for example, black paint or tape.

System 100 may further include a transparent overlay applicator 140 that may apply a fluid, liquid, or other transparent overlay to target material 125 over the portion coated by material applicator 135. The transparent overlay material may be substantially transparent to the radiation. For example, the transparent overlay material may be flowing water or clear tape.

As shown in FIG. 1, both material applicator 135 and transparent overlay material applicator 140 are shown directly located within target chamber 105. Of course, in some embodiments, only the operative portions of material applicator 135 and transparent overlay material applicator 140 are located through and within target chamber 105, such as the portion through which the materials actually flow through a flow head. The supply tanks for the transparent overlay material and the opaque material may be located outside of target chamber 105.

A control unit, such as controller 145, may be operatively associated with each of the material applicator 135, transparent overlay material applicator 140, laser 120, and positioning mechanism 130 to ensure proper sequencing and timing of system 100. As shown in FIG. 1, controller 145 may be connected to laser 120, positioning mechanism 130, material applicator 135, and transparent overlay material applicator 140 via control lines 150, 155, 160, and 165, respectively. Controller 145, in one embodiment, may be a programmable personal computer or microprocessor. In operation, controller 145 may control the operation of system 100 once initiated.

System 100 may also include a detector (not shown). The detector may be configured to detect damage in at least one of a back surface of the article and within the article. The detector may be, for example, an ultrasonic detector, a camera, image analysis techniques, including cameras with manual or automated software that provide quantitative metrics about captured images, optical or laser interference profilometry, such as three dimensional vision systems that can measure depth and volume of cavities using interference methods, and precision weighing of ejected material. In some embodiments of system 100, a mechanical detector may not be present. Instead, an operator may simply view the article after processing to determine the existence and/or the extent of any damage to the article.

Figure 2:
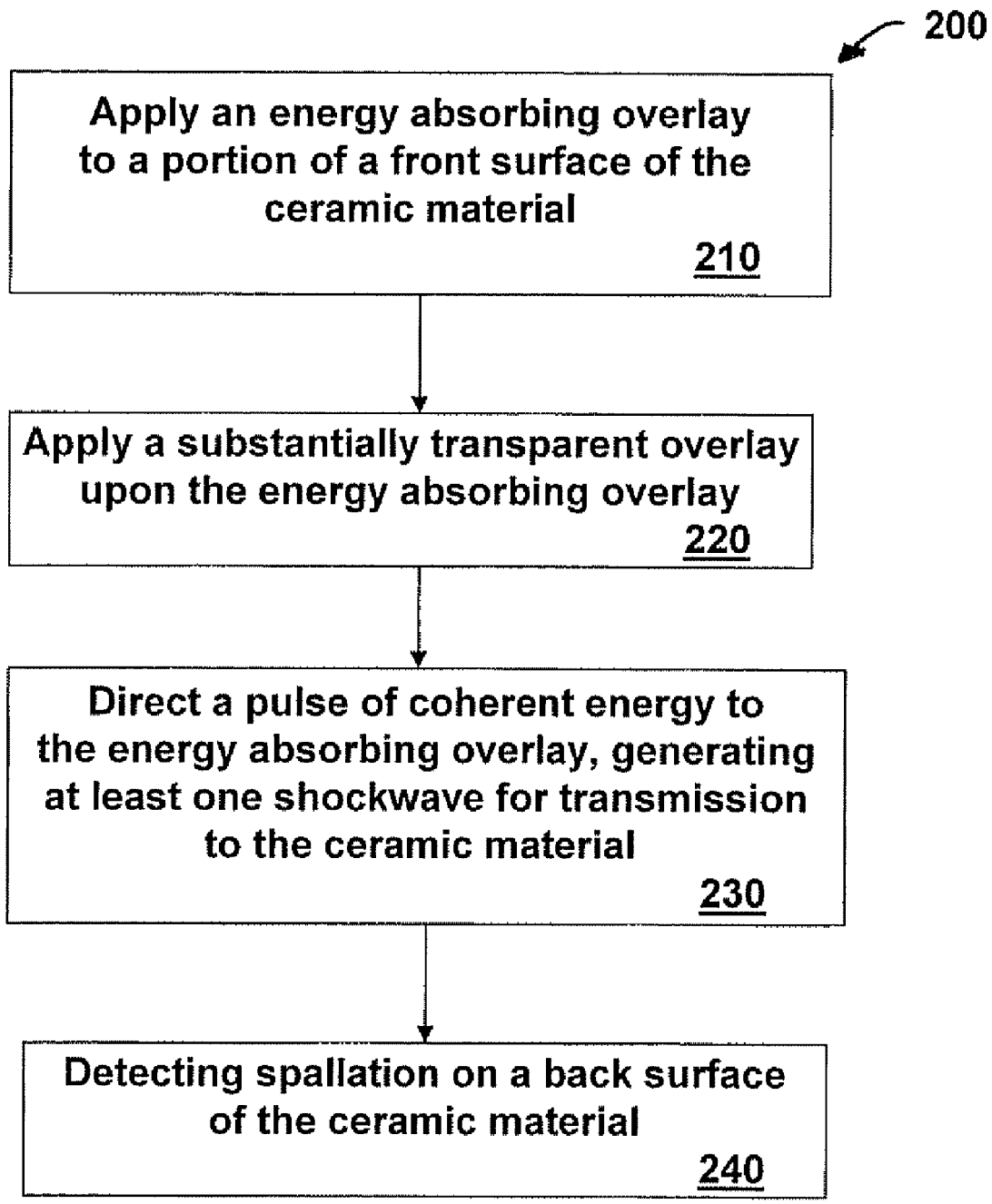
FIG. 2 is an exemplary flow chart for a method of evaluating impact resistance of a ceramic material.

With reference to FIG. 2, a system such as system 100 may be used to carry out a method 200 of evaluating impact resistance of a ceramic material. For example, material applicator 135 may apply an energy absorbing overlay to a portion of a front surface of the ceramic material (210). Transparent overlay material applicator 140 may apply a substantially transparent overlay upon the energy absorbing overlay (220). Laser 120 may direct a pulse of coherent energy in the form of laser beam 115 to the energy absorbing overlay, generating at least one shockwave for transmission to the ceramic material (230). Spallation may be detected on a back surface of the ceramic material (240).

Figure 3:
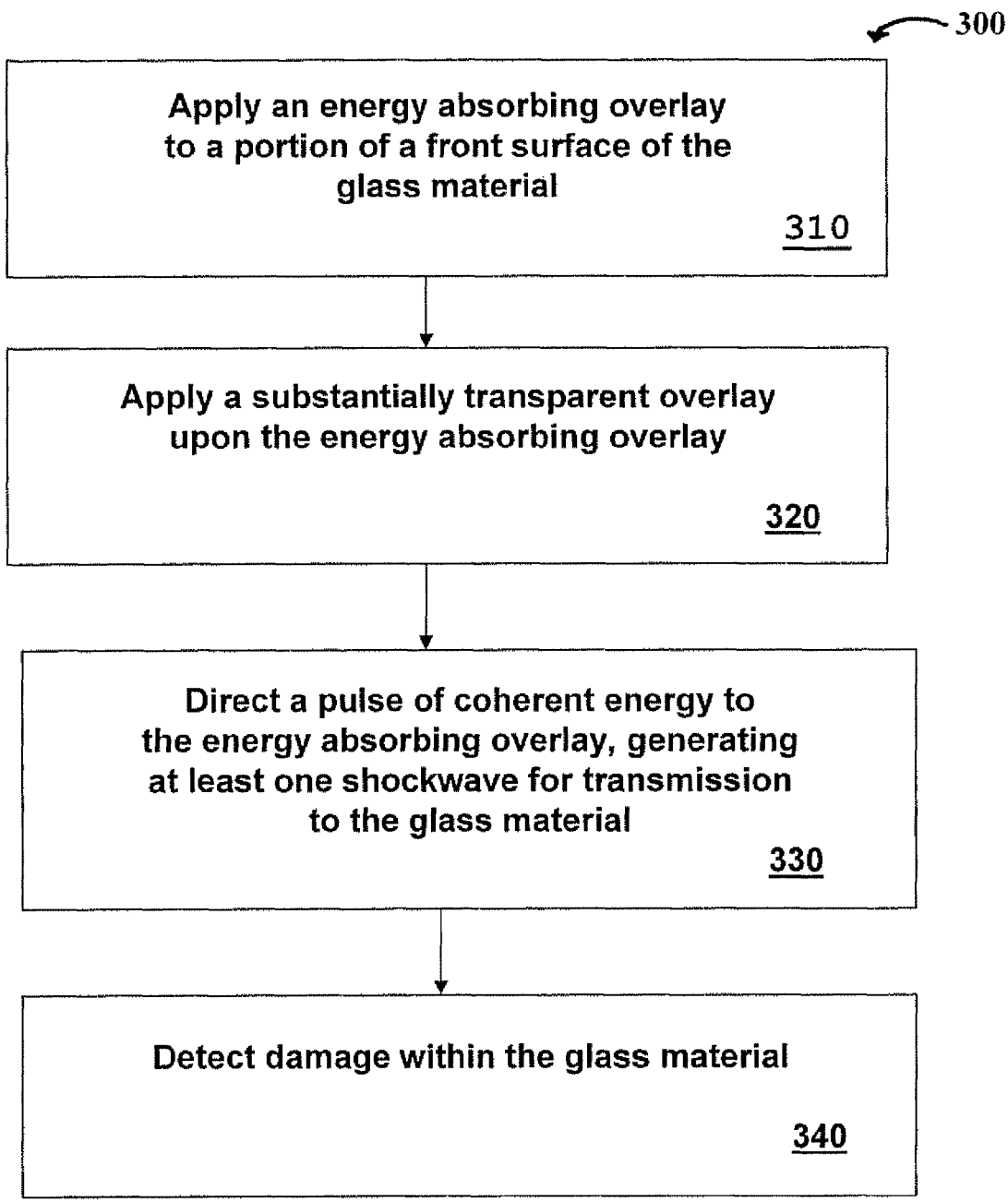
FIG. 3 is an exemplary flow chart for a method of evaluating impact resistance of a glass material.

With reference to FIG. 3, a system such as system 100 may be also be used to carry out a method 300 of evaluating impact resistance of a glass material. For example, material applicator 135 may apply an energy absorbing overlay to a portion of a front surface of the glass material (310). Transparent overlay material applicator 140 may apply a substantially transparent overlay upon the energy absorbing overlay (320). Laser 120 may direct a pulse of coherent energy in the form of laser beam 115 to the energy absorbing overlay, generating at least one shockwave for transmission to the glass material (330). Damage may be detected within the glass material (340).

Figure 4:
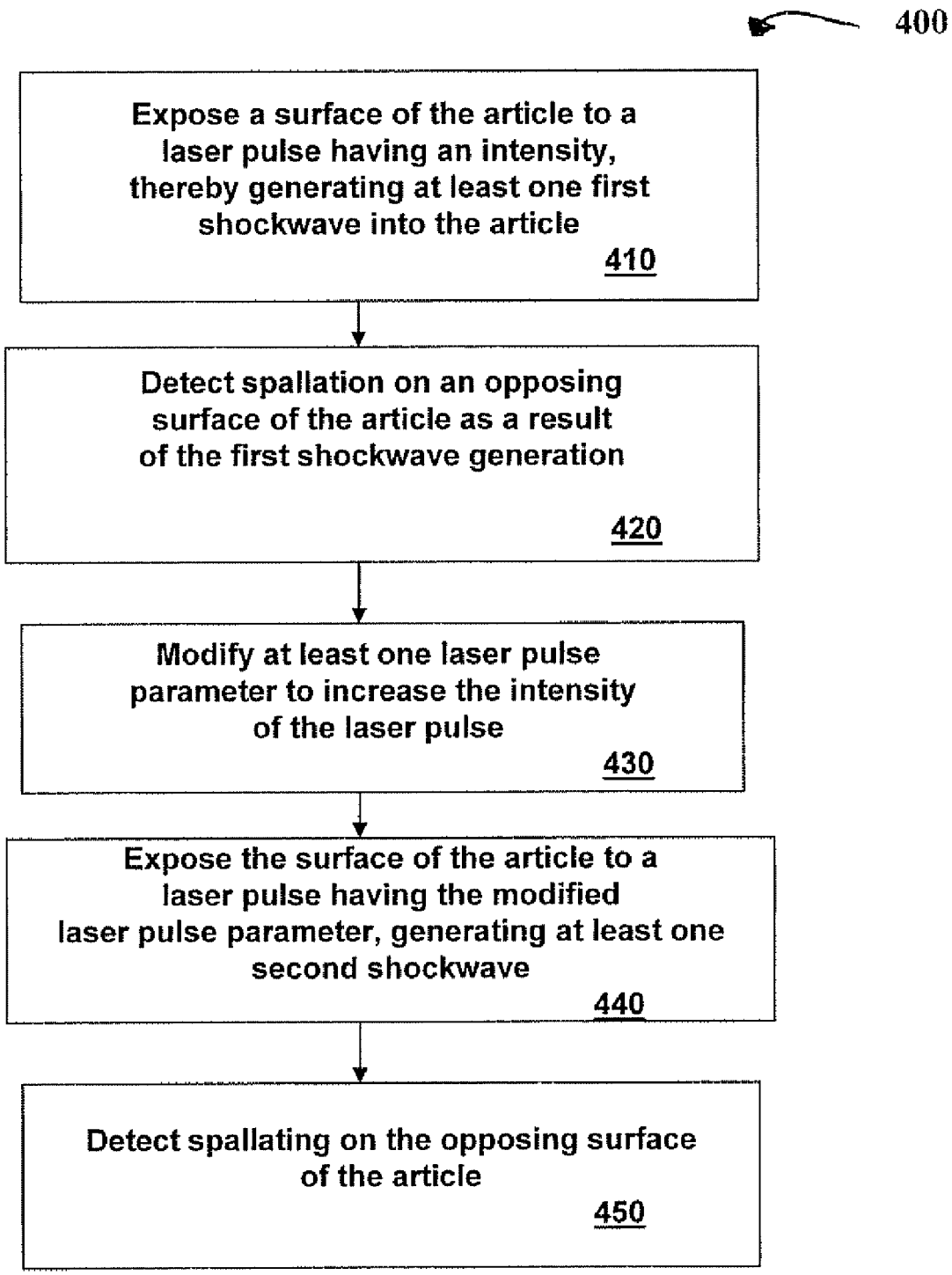
FIG. 4 is an exemplary flow chart for a method of identifying a threshold energy for damage to an article.

With reference to FIG. 4, a system such as system 100 may be also be used to carry out a method 400 of identifying a threshold energy for damage to an article. For example, laser source 120 may expose a surface of the article to a laser pulse having an intensity, thereby generating at least one first shockwave into the article (410). Spallation may be detected on an opposing surface of the article as a result of the first shockwave generation (420). At least one laser pulse parameter may be modified to increase the intensity of the laser pulse (430). The surface of the article may be exposed to a laser pulse having the modified laser pulse parameter, generating at least one second shockwave (440). Spallation may then be detected on the opposing surface of the article (450).

Figure 5:
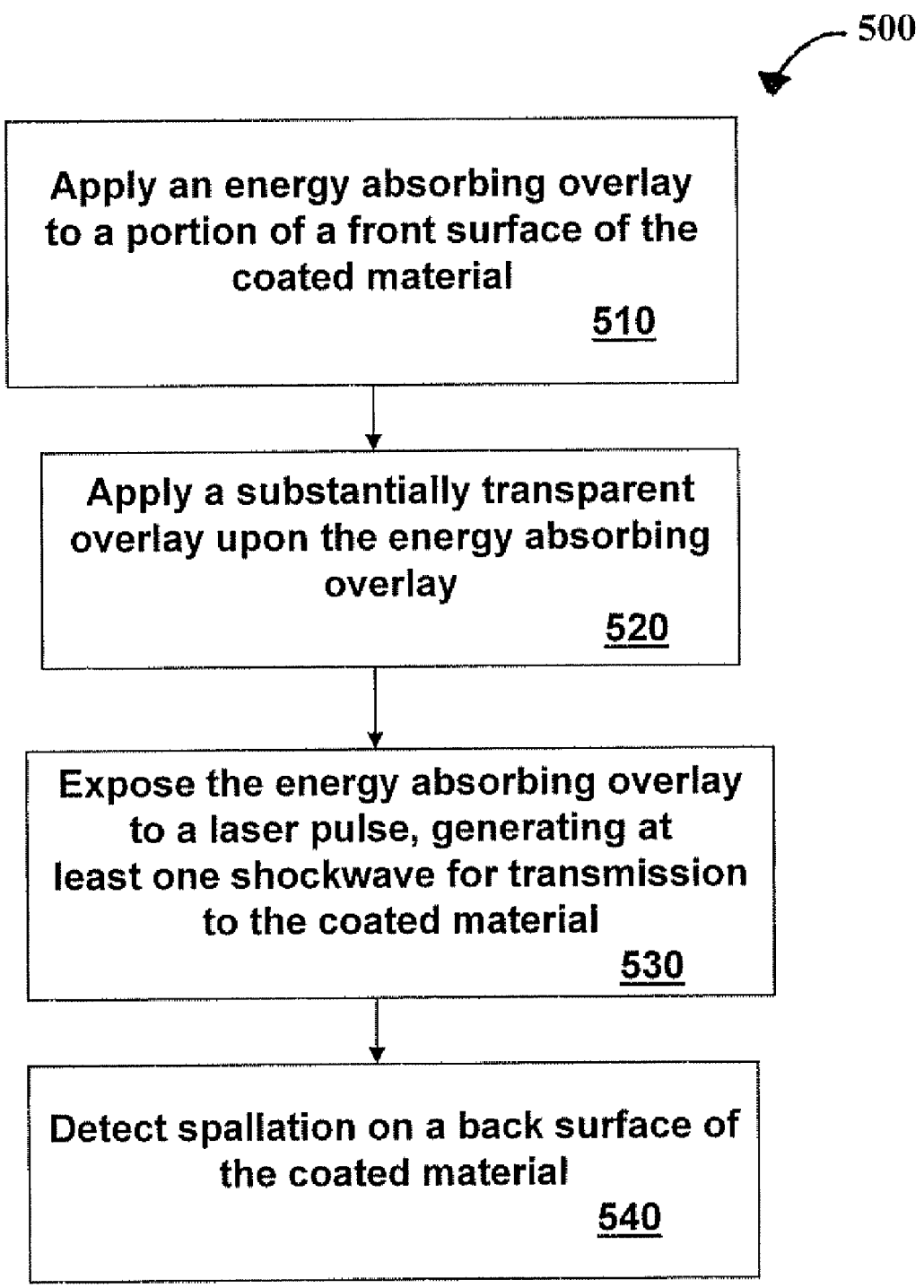
FIG. 5 is an exemplary flow chart for a method of testing the adhesion of a coating on a coated material.

With reference to FIG. 5, a system such as system 100 may be also be used to carry out a method 500 of testing the adhesion of a coating on a coated material. For example, material applicator 135 may apply an energy absorbing overlay to a portion of a front surface of the coated material (510). Transparent overlay material applicator 140 may apply a substantially transparent overlay upon the energy absorbing overlay (520). Laser source 120 may expose the energy absorbing overlay to a laser pulse, generating at least one shockwave for transmission to the coated material (530). Spallation may be detected on a back surface of the coated material (540).

As described with reference to FIG. 2 and FIG. 3, methods are provided for evaluating impact resistance of ceramic and glass materials. The laser generated shock waves simulate ballistic impact in the materials. The methods are quick and cost effective, and lend themselves to use as a development and quality control tool during optimization and production in armor tiles. Generally speaking, shock waves are transmitted to the front face of a ceramic or glass tile and travel through the tile as compression waves. The shock waves reflect as a tensile wave off of the back surface of the tile.

In the case of ceramic tile, spallation damage may occur on the back surface of the tile. Spallation damage may be characterized in terms of damage diameter and depth, and may be correlated to laser pulse parameters, such as laser spot diameter, laser beam energy, temporal pulse duration, and the resulting laser fluence. The depth of spallation defects and the spall diameter may also correlate to thickness of the sample.

Figure 6:
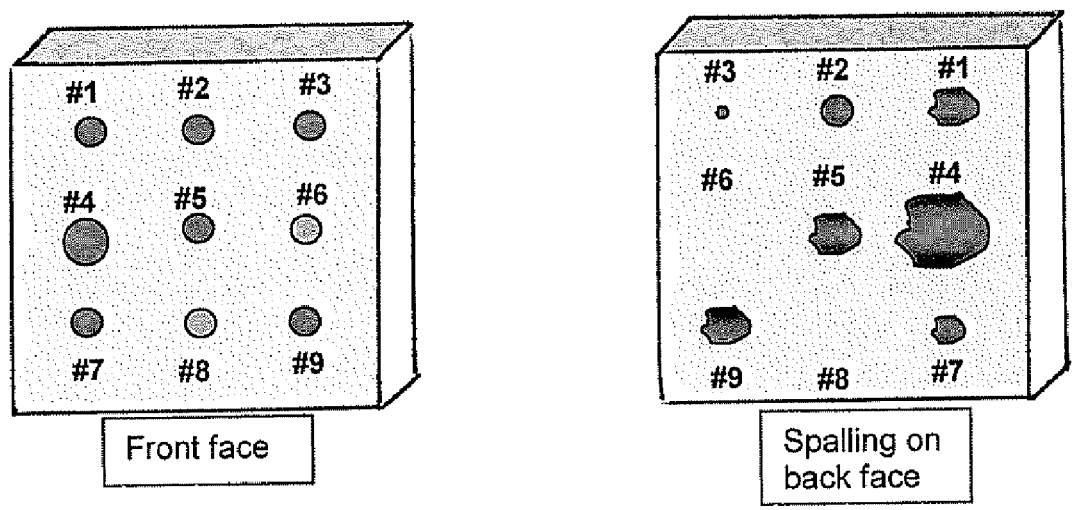
FIG. 6 illustrates front and back views of a 100 mm×100 mm×0.30 mm silicon carbide sample which has been laser shock processed under various laser pulse parameters.

FIG. 6 illustrates front and back views of a 100 mm×100 mm×30 mm silicon carbide sample that was laser shock processed under various laser pulse parameters. As shown in Table 1, a range of laser pulse intensities and conditions were evaluated to demonstrate the range of damage (in this case, back face spalling) that may be achieved when using laser shocks to simulate ballistic impact events.

TABLE 1

| Location No. | Energy (J) | Pulse Duration (ns) | Spot Diameter (mm) | Power Density (GW/cm$^2$) | Opaque Overlay | No. of Shots |
|---|---|---|---|---|---|---|
| 1 | 20 | 20 | 5.6 | 4.1 | Tape | 1 |
| 2 | 22 | 22 | 5.6 | 4.1 | No Tape | 1 |
| 3 | 10.7 | 20 | 5.6 | 2.1 | Tape | 1 |
| 4 | 41 | 15.5 | 7.4 | 6.2 | Tape | 1 |
| 5 | 41 | 18.4 | 5.6 | 8.9 | Tape | 1 |
| 6 | | | Not Tested | | | |
| 7 | 15.2 | 21.4 | 5.6 | 2.84 | Tape | 1 |
| 8 | | | Not Tested | | | |
| 9 | 20 | 20 | 5.6 | 4.1 | Tape | 3 |

The spot locations of FIG. 6 were processed as follows. First, location #5 was processed using a high intensity condition, anticipating that this condition would cause the most spalling damage. The resulting spalled area on the back face of the tile was approximately 8 mm in diameter and approximately 0.25 mm deep. Location #1 was processed next, using about half the power density of that used for location. The resulting spalled area was about 7 mm in diameter and 0.15 mm deep. Location #3 was then processed using half the power density used for location #1. Only a small blister appeared on the back face, indicating that 2 GW/cm² is about the threshold power density for causing damage to the tile depicted in FIG. 6. Location #7 was then processed with a power density about half way between that used for location #3 and #1. The spalled area was about 4 mm in diameter and about 0.1 mm deep. Location #9 was processed using the same conditions as location #1, but using 3 shots. The spalled area was 7-8 mm in diameter and increased in depth with each shot from about 0.15 mm to 0.25 mm to 0.45 mm deep. Location 42 was processed using the same laser conditions as used for location #1, except that no opaque overlay (tape) was used. The spalled area was slightly smaller in diameter (~6 mm) and about 0.15 mm deep. The front face was darkened from the contact with the plasma. Location #4 was processed using a larger spot diameter (7.4 mm). The spalled area was considerably larger (~12 mm diameter and 0.15 to 0.5 mm deep). This spalled area had a convex crater (i.e., shallowest in the center and deepest at the perimeter).

Generally speaking, no damage occurred on the front face with the exception of a plasma mark when no tape was used (location #2). Most of the spalling marks had a relatively flat bottom or slightly concave profile. As noted above, the spall at location #4 with the large diameter spot had a convex profile. The spalling damage had a diameter of about 40-60% larger than the laser beam spot size. This data may suggest that the shock wave remains fairly planar as it progresses through the sample. The depth of the spalling damage was quite shallow (0.1 mm-0.5 mm). The power density threshold for spalling damage was about 2 GW/cm² using the 5.6 mm spot size. The extent of spalling was more sensitive to spot size than to the laser intensity changes tested. Multiple shots were shown to increase the depth of spalling with a nearly linear relationship. More severe damage may be achieved using a large spot size and multiple shots.

For the boron carbide samples processed as shown in FIG. 7 through FIG. 10, a nominal spot diameter of 5.0 mm and a nominal pulse duration of 20 ns were selected for all laser spots. The beam energy was varied. The depth of the spallation defects and the spall diameter correlate reproducibly with the laser fluence and the thickness of the sample.

Figure 7:
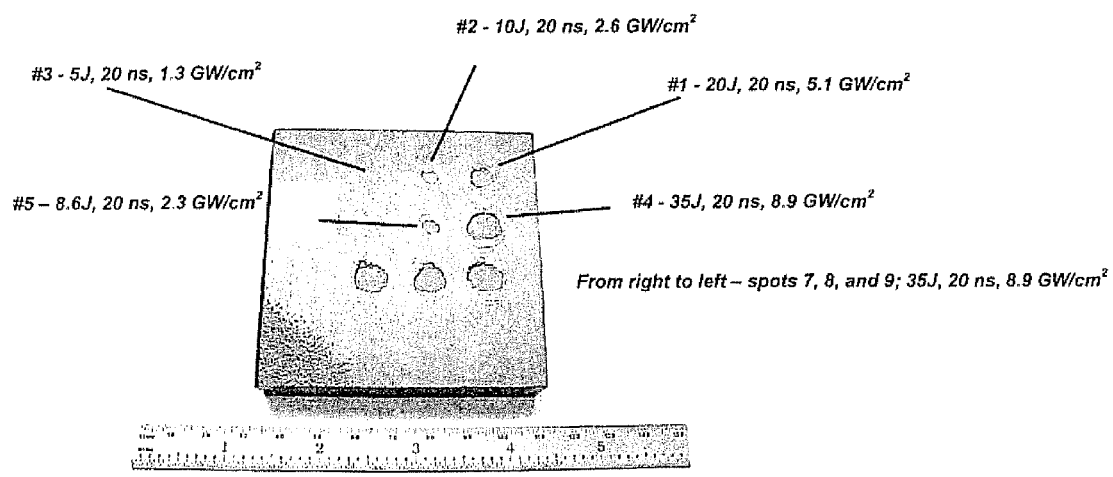
FIG. 7 illustrates a back view of a 3"×3"×0.600" thick boron carbide sample which has been laser shock processed under various laser pulse parameters as an initial scoping sample.

FIG. 7 illustrates a back view of a 3"×3"×0.600" thick boron carbide sample which has been laser shock processed under various laser pulse parameters as an initial scoping sample. Table 2 illustrates the experimental matrix.

TABLE 2

| Location No. | Energy (J) | Pulse Duration (ns) | Spot Diameter (mm) | Power Density (GW/cm²) | Opaque Overlay | No. of Shots |
|---|---|---|---|---|---|---|
| 1 | 20 | 20 | 5.0 | 5.1 | Tape | 1 |
| 2 | 10 | 20 | 5.0 | 2.6 | Tape | 1 |
| 3 | 5 | 20 | 5.0 | 1.3 | Tape | 1 |
| 4 | 35 | 20 | 5.0 | 8.9 | Tape | 1 |
| 5 | 8.6 | 20 | 5.0 | 2.3 | Tape | 1 |
| 6 | | | Not Tested | | | |
| 7 | 35 | 20 | 5.0 | 8.9 | Tape | 1 |
| 8 | 35 | 20 | 5.0 | 8.9 | Tape | 1 |
| 9 | 35 | 20 | 5.0 | 8.9 | Tape | 1 |

Figure 8:
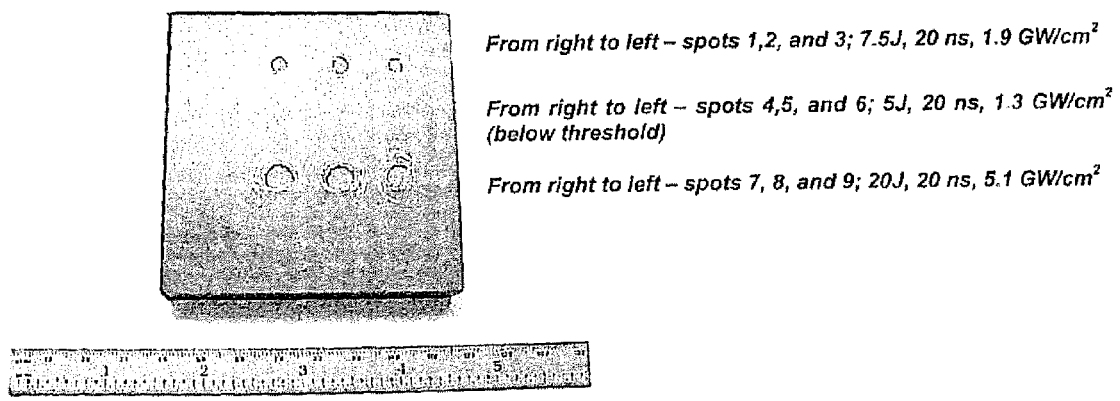
FIG. 8 illustrates a back view of a 3"×3"×0.600" thick boron carbide sample which has been laser shock processed under various laser pulse parameters as a spallation threshold test.

FIG. 8 illustrates a back view of a 3"×3"×0.600" thick boron carbide sample which has been laser shock processed under various laser pulse parameters as a spallation threshold test. Table 3 illustrates the experimental matrix.

TABLE 3

| Location No. | Energy (J) | Pulse Duration (ns) | Spot Diameter (mm) | Power Density (GW/cm²) | Opaque Overlay | No. of Shots |
|---|---|---|---|---|---|---|
| 1 | 7.5 | 20 | 5.0 | 1.9 | Tape | 1 |
| 2 | 7.5 | 20 | 5.0 | 1.9 | Tape | 1 |
| 3 | 7.5 | 20 | 5.0 | 1.9 | Tape | 1 |
| 4 | 5 | 20 | 5.0 | 1.3 | Tape | 1 |
| 5 | 5 | 20 | 5.0 | 1.3 | Tape | 1 |
| 6 | 5 | 20 | 5.0 | 1.3 | Tape | 1 |
| 7 | 20 | 20 | 5.0 | 5.1 | Tape | 1 |
| 8 | 20 | 20 | 5.0 | 5.1 | Tape | 1 |
| 9 | 20 | 20 | 5.0 | 5.1 | Tape | 1 |

Figure 9:
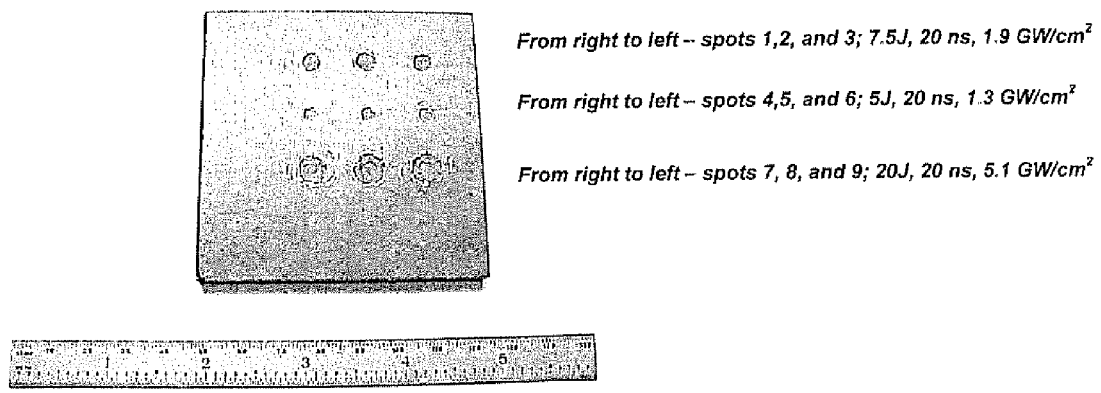
FIG. 9 illustrates a back view of a 3"×3"×0.300" thick boron carbide sample which has been laser shock processed under various laser pulse parameters as a spallation threshold test.

FIG. 9 illustrates a back view of a 3"×3"×0.300" thick boron carbide sample which has been laser shock processed under various laser pulse parameters as a spallation threshold test. Table 4 illustrates the experimental matrix.

TABLE 4

| Location No. | Energy (J) | Pulse Duration (ns) | Spot Diameter (mm) | Power Density (GW/cm²) | Opaque Overlay | No. of Shots |
|---|---|---|---|---|---|---|
| 1 | 7.5 | 20 | 5.0 | 1.9 | Tape | 1 |
| 2 | 7.5 | 20 | 5.0 | 1.9 | Tape | 1 |
| 3 | 7.5 | 20 | 5.0 | 1.9 | Tape | 1 |
| 4 | 5 | 20 | 5.0 | 1.3 | Tape | 1 |
| 5 | 5 | 20 | 5.0 | 1.3 | Tape | 1 |
| 6 | 5 | 20 | 5.0 | 1.3 | Tape | 1 |
| 7 | 20 | 20 | 5.0 | 5.1 | Tape | 1 |
| 8 | 20 | 20 | 5.0 | 5.1 | Tape | 1 |
| 9 | 20 | 20 | 5.0 | 5.1 | Tape | 1 |

Figure 10:
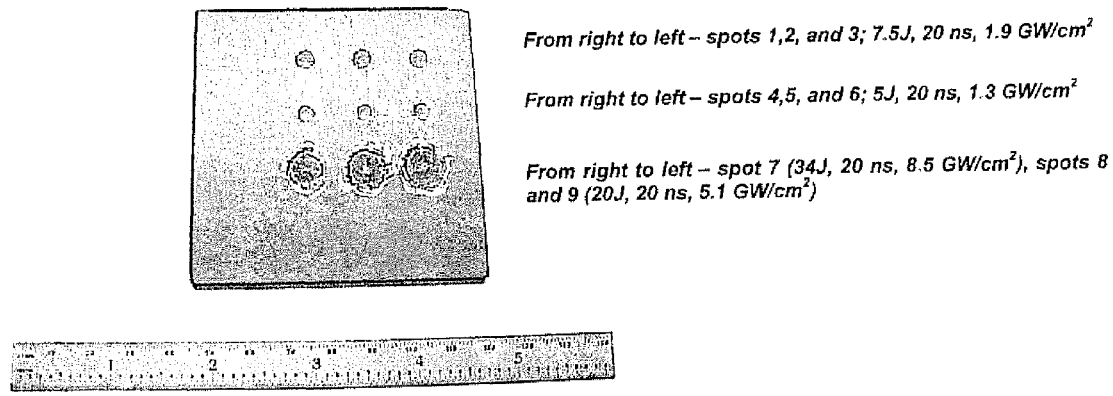
FIG. 10 illustrates a back view of a 3"×3"×0.150" thick boron carbide sample which has been laser shock processed under various laser pulse parameters as a spallation threshold test.

FIG. 10 illustrates a back view of a 3"×3"×0.150" thick boron carbide sample which has been laser shock processed under various laser pulse parameters as a spallation threshold test. Table 5 illustrates the experimental matrix.

TABLE 5

| Location No. | Energy (J) | Pulse Duration (ns) | Spot Diameter (mm) | Power Density (GW/cm²) | Opaque Overlay | No. of Shots |
|---|---|---|---|---|---|---|
| 1 | 7.5 | 20 | 5.0 | 1.9 | Tape | 1 |
| 2 | 7.5 | 20 | 5.0 | 1.9 | Tape | 1 |
| 3 | 7.5 | 20 | 5.0 | 1.9 | Tape | 1 |
| 4 | 5 | 20 | 5.0 | 1.3 | Tape | 1 |
| 5 | 5 | 20 | 5.0 | 1.3 | Tape | 1 |
| 6 | 5 | 20 | 5.0 | 1.3 | Tape | 1 |
| 7 | 34 | 20 | 5.0 | 8.5 | Tape | 1 |
| 8 | 20 | 20 | 5.0 | 5.1 | Tape | 1 |
| 9 | 20 | 20 | 5.0 | 5.1 | Tape | 1 |

As demonstrated in FIGS. 6-10, the laser shock spallation methods offer excellent reproducibility and controllability in ceramic tiles, and the laser pulse test parameters may be varied easily to establish the threshold conditions where damage occurs. This controllability may be useful for optimizing the performance of new ceramic materials, and for routine quality control testing or comparison of products from various suppliers.

In the case of glass tiles, material is typically not ejected from the back face of the glass tile. Rather, the damage is typically observed visually as a fine network of shattered cracks inside the glass. The extent of the damage may be quantified photographically or using ultrasonic inspection techniques.

Figure 11:
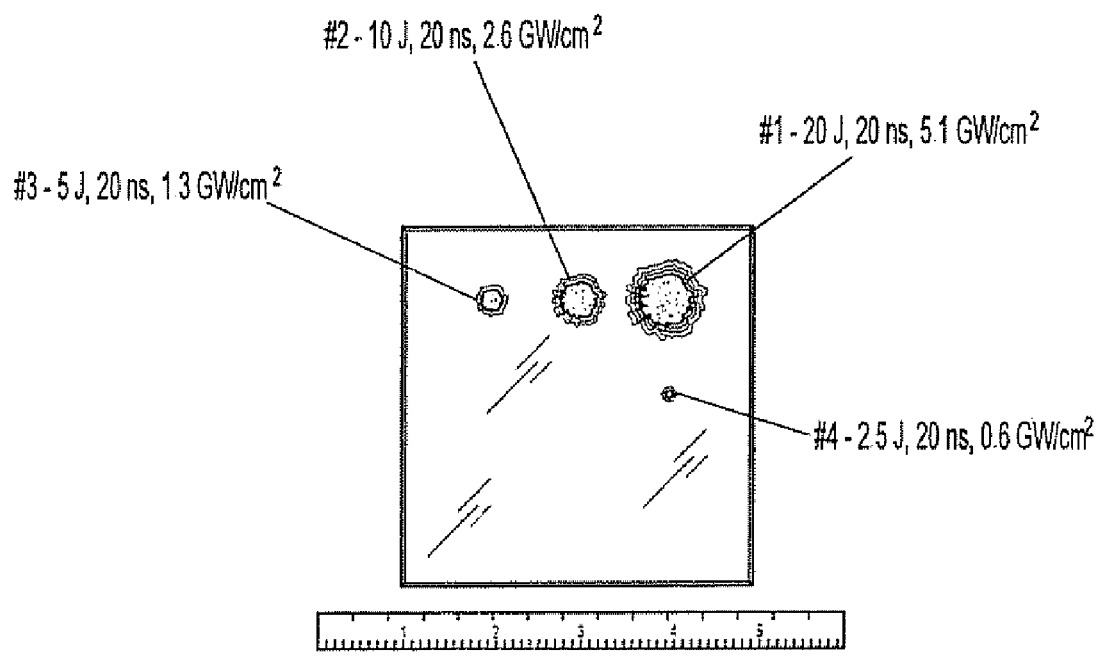
FIG. 11 illustrates a 4"×4"×0.25" thick borosilicate glass sample which has been laser shock processed under various laser pulse parameters as an initial scoping sample.

FIG. 11 illustrates a 4"×4"×0.25" thick borosilicate glass sample which has been laser shock processed under various laser pulse parameters as an initial scoping sample. Table 6 illustrates the experimental matrix.

TABLE 6

| Location No. | Energy (J) | Pulse Duration (ns) | Spot Diameter (mm) | Power Density (GW/cm$^2$) | Opaque Overlay | No. of Shots |
|---|---|---|---|---|---|---|
| 1 | 20 | 20 | 5.0 | 5.1 | Tape | 1 |
| 2 | 10 | 20 | 5.0 | 2.6 | Tape | 1 |
| 3 | 5 | 20 | 5.0 | 1.3 | Tape | 1 |
| 4 | 2.5 | 20 | 5.0 | 0.6 | Tape | 1 |

Figure 12:
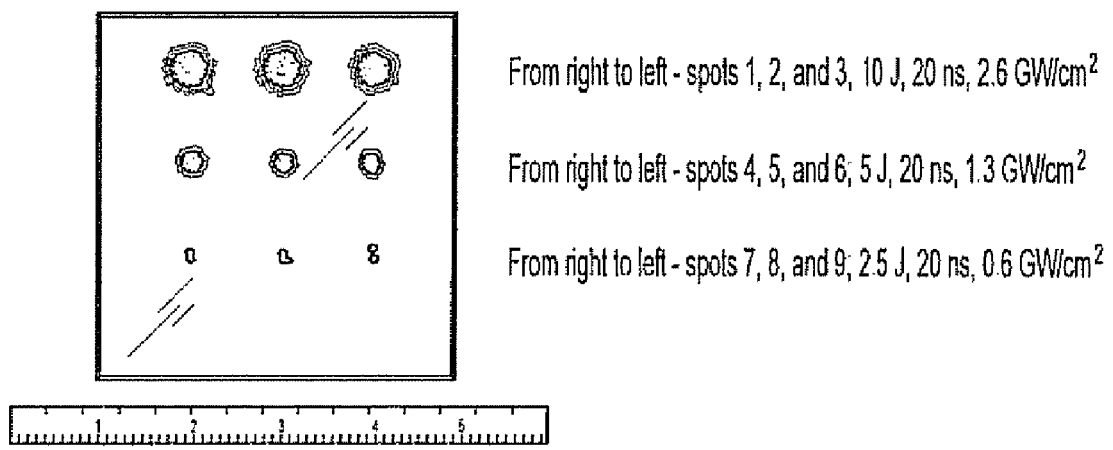
FIG. 12 illustrates a 4"×4"×0.25" thick borosilicate glass sample which has been laser shock processed under various laser pulse parameters as a spallation threshold test.

FIG. 12 illustrates a 4"×4"×0.25" thick borosilicate glass sample which has been laser shock processed under various laser pulse parameters as a spallation threshold test. Table 7 illustrates the experimental matrix.

TABLE 7

| Location No. | Energy (J) | Pulse Duration (ns) | Spot Diameter (mm) | Power Density (GW/cm$^2$) | Opaque Overlay | No. of Shots |
|---|---|---|---|---|---|---|
| 1 | 10 | 20 | 5.0 | 2.6 | Tape | 1 |
| 2 | 10 | 20 | 5.0 | 2.6 | Tape | 1 |
| 3 | 10 | 20 | 5.0 | 2.6 | Tape | 1 |
| 4 | 5 | 20 | 5.0 | 1.3 | Tape | 1 |
| 5 | 5 | 20 | 5.0 | 1.3 | Tape | 1 |
| 6 | 5 | 20 | 5.0 | 1.3 | Tape | 1 |
| 7 | 2.5 | 20 | 5.0 | 0.6 | Tape | 1 |
| 8 | 2.5 | 20 | 5.0 | 0.6 | Tape | 1 |
| 9 | 2.5 | 20 | 5.0 | 0.6 | Tape | 1 |

Figure 13:
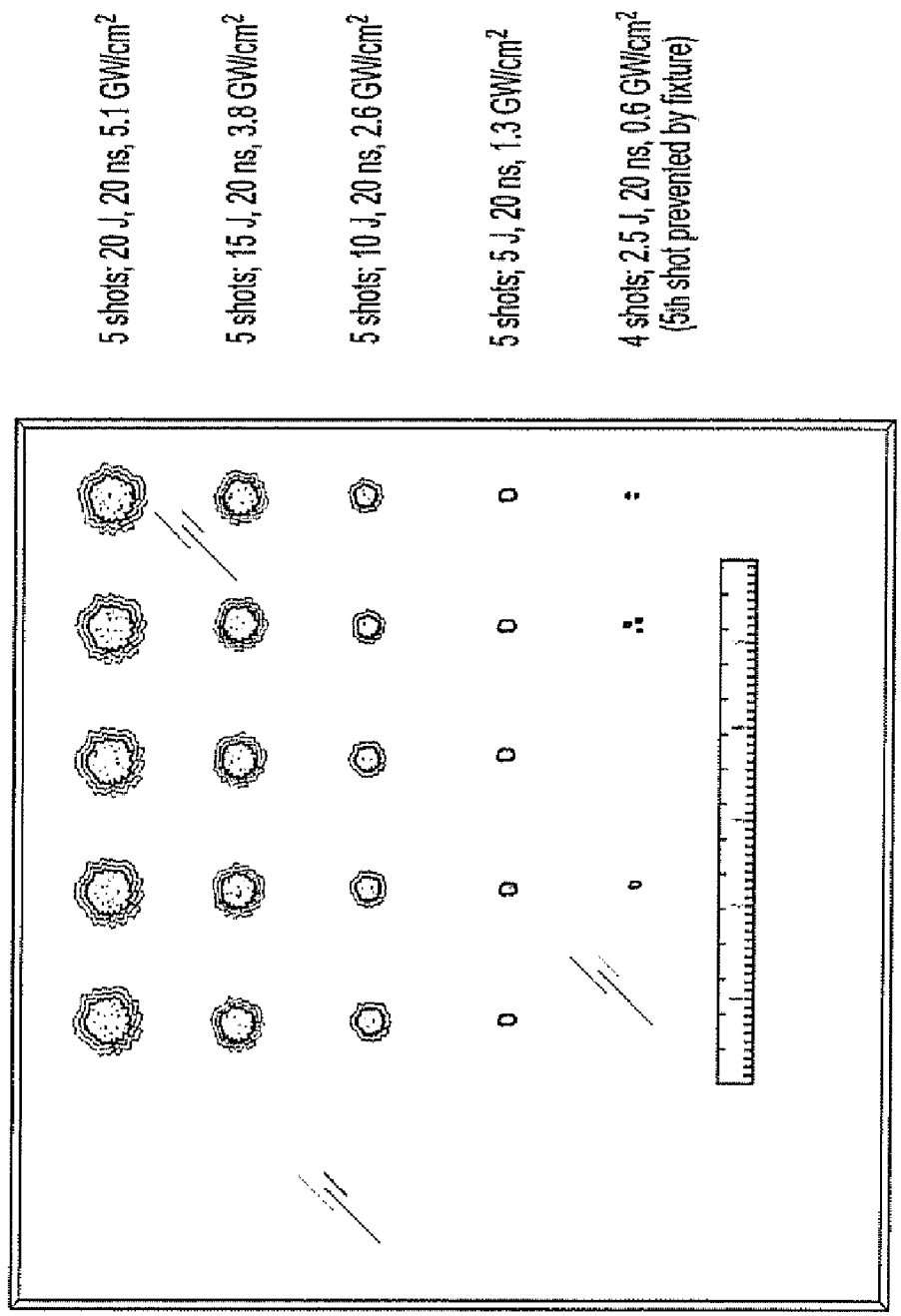
FIG. 13 illustrates a 10"×10"×0.375" thick borosilicate glass sample which has been laser shock processed under various laser pulse parameters as a spallation reproducibility test.

FIG. 13 illustrates a 10"×10"×0.375" thick borosilicate glass sample which has been laser shock processed under various laser pulse parameters as a spallation reproducibility test. Table 8 illustrates the experimental matrix. Row 1 is the top line. Each location was given one (1) shot, with multiple shots in a row.

TABLE 8

| Location No. | Energy (J) | Pulse Duration (ns) | Spot Diameter (mm) | Power Density (GW/cm$^2$) | Opaque Overlay | No. of Shots |
|---|---|---|---|---|---|---|
| Row 1 | 20 | 20 | 5.0 | 5.1 | Tape | 1 |
| Row 2 | 15 | 20 | 5.0 | 3.8 | Tape | 1 |
| Row 3 | 10 | 20 | 5.0 | 2.6 | Tape | 1 |
| Row 4 | 5 | 20 | 5.0 | 1.3 | Tape | 1 |
| Row 5 | 2.5 | 20 | 5.0 | 0.6 | Tape | 1 |

Figure 14:
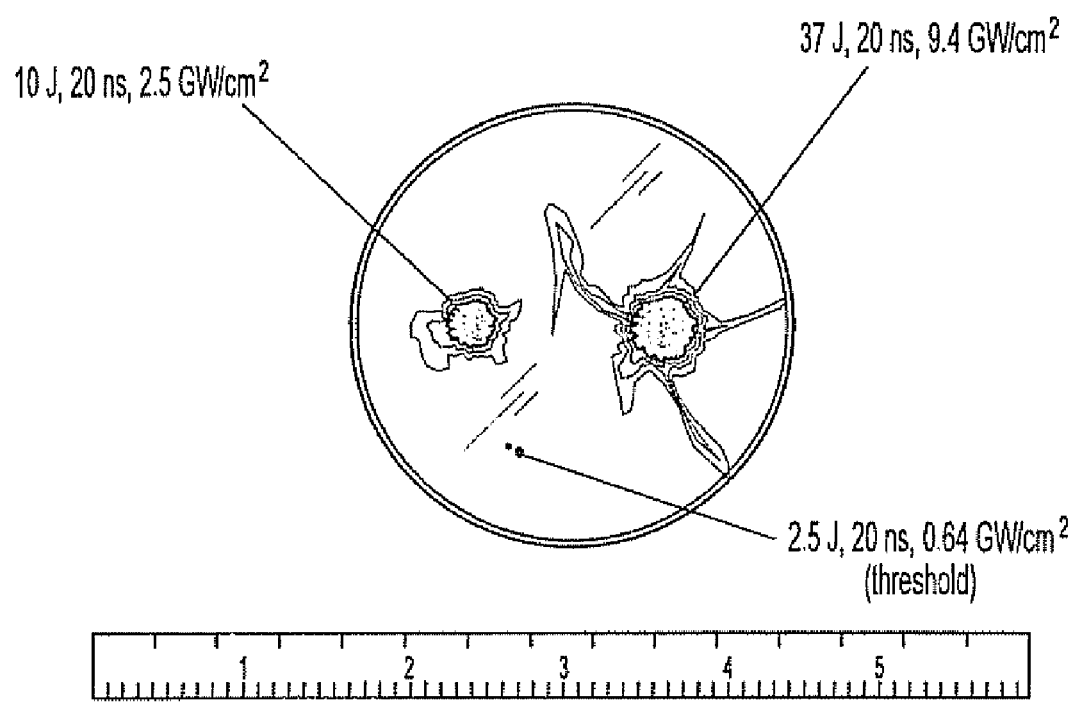
FIG. 14 illustrates a 2.5" diameter×0.25" thick soda lime glass sample which has been laser shock processed under various laser pulse parameters as a spallation threshold test.

FIG. 14 illustrates a 2.5" diameter×0.25" thick soda lime glass sample which has been laser shock processed under various laser pulse parameters as a spallation threshold test. Table 9 illustrates the experimental matrix.

TABLE 9

| Location No. | Energy (J) | Pulse Duration (ns) | Spot Diameter (mm) | Power Density (GW/cm$^2$) | Opaque Overlay | No. of Shots |
|---|---|---|---|---|---|---|
| 1 | 37 | 20 | 5.0 | 9.4 | Tape | 1 |
| 2 | 10 | 20 | 5.0 | 2.5 | Tape | 1 |
| 3 | 2.5 | 20 | 5.0 | 0.64 | Tape | 1 |

Figure 15:
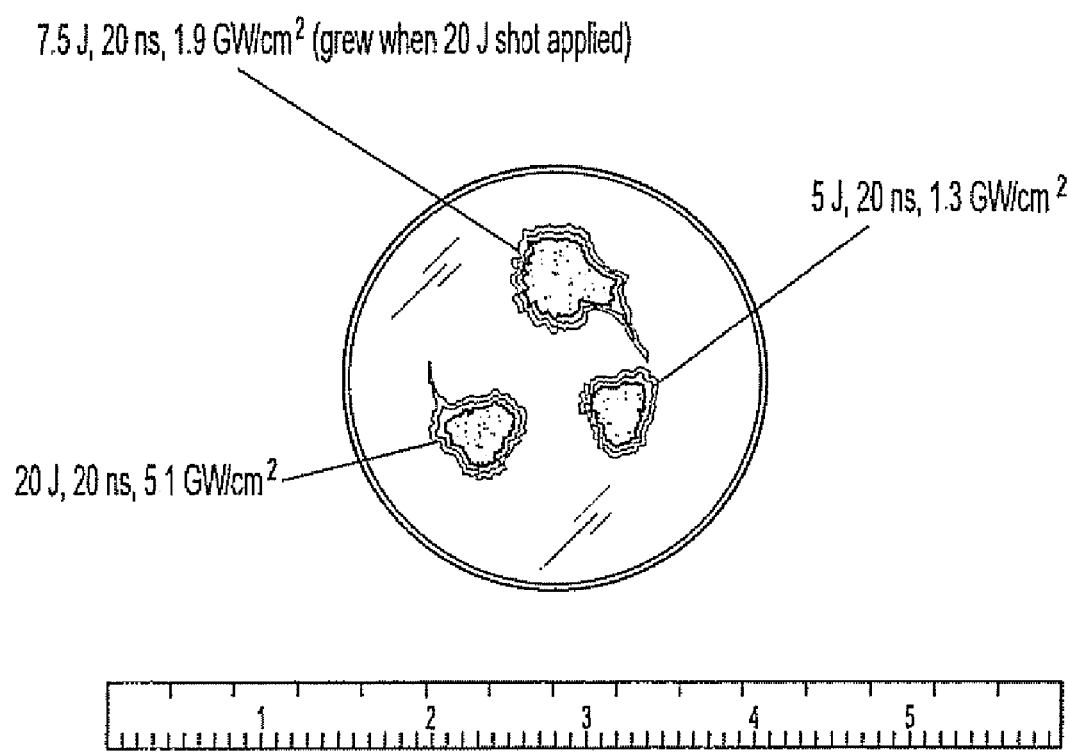
FIG. 15 illustrates a 2.5" diameter×0.25" thick soda lime glass sample which has been laser shock processed under various laser pulse parameters as a spallation threshold test.

FIG. 15 illustrates a 2.5" diameter×0.25" thick soda lime glass sample which has been laser shock processed under various laser pulse parameters as a spallation threshold test. Table 10 illustrates the experimental matrix.

TABLE 10

| Location No. | Energy (J) | Pulse Duration (ns) | Spot Diameter (mm) | Power Density (GW/cm$^2$) | Opaque Overlay | No. of Shots |
|---|---|---|---|---|---|---|
| 1 | 5 | 20 | 5.0 | 1.3 | Tape | 1 |
| 2 | 7.5 | 20 | 5.0 | 1.9 | Tape | 1 |
| 3 | 20 | 20 | 5.0 | 5.1 | Tape | 1 |

Figure 16:
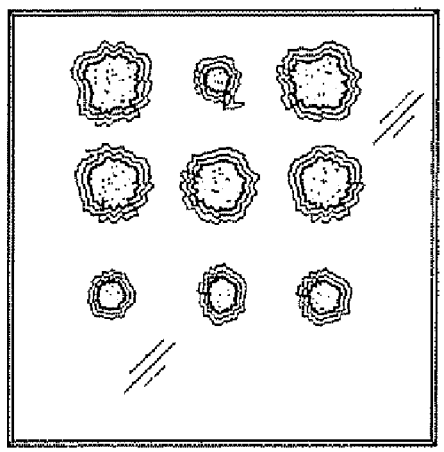
FIG. 16 illustrates a rear view of a 4"×4"×0.25" thick, double pane borosilicate glass sample which has been laser shock processed under various laser pulse parameters as an interface spallation test.
Figure 17:
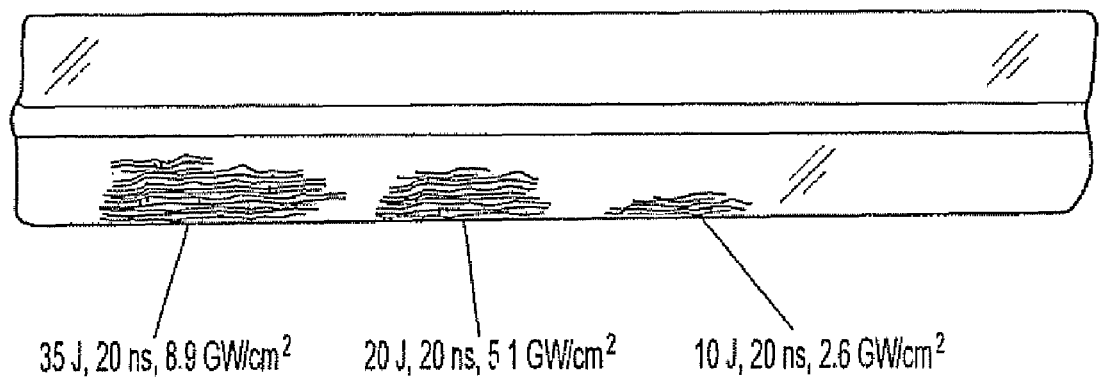
FIG. 17 illustrates a cross-sectional view of a 4"×4"×0.25" thick, double pane borosilicate glass sample which has been laser shock processed under various laser pulse parameters as an interface spallation test.

FIG. 16 illustrates a frontal view of a 4"×4"×0.25" thick, double pane borosilicate glass sample which has been laser shock processed under various laser pulse parameters as an interface spallation test. FIG. 17 illustrates a side view of the sample. Table 11 illustrates the experimental matrix.

TABLE 11

| Location No. | Energy (J) | Pulse Duration (ns) | Spot Diameter (mm) | Power Density (GW/cm$^2$) | Opaque Overlay | No. of Shots |
|---|---|---|---|---|---|---|
| 1 | 35 | 20 | 5.0 | 8.9 | Tape | 1 |
| 2 | 35 | 20 | 5.0 | 8.9 | Tape | 1 |
| 3 | 35 | 20 | 5.0 | 8.9 | Tape | 1 |
| 4 | 20 | 20 | 5.0 | 5.1 | Tape | 1 |
| 5 | 20 | 20 | 5.0 | 5.1 | Tape | 1 |
| 6 | 20 | 20 | 5.0 | 5.1 | Tape | 1 |
| 7 | 10 | 20 | 5.0 | 2.6 | Tape | 1 |
| 8 | 10 | 20 | 5.0 | 2.6 | Tape | 1 |
| 9 | 10 | 20 | 5.0 | 2.6 | Tape | 1 |

As demonstrated in FIGS. 11-47, the laser shock spallation methods also offer excellent reproducibility and controllability in glass tiles. No material was ejected from the back face of the samples. Instead, the samples shattered internally, and the glass captured the shock wave event as a three dimensional record. The internal damage correlates well to the intensity of the laser shocking. The laser pulse test parameters may be varied easily to establish the threshold conditions where damage occurs. This controllability may be useful for optimizing the performance of new glass materials, and for routine quality control testing or comparison of products from various suppliers.

The laser shock spallation methods may be more controllable, more sensitive, faster, and less expensive than traditional ballistic methods. For instance, the shock wave generated by the laser pulse typically propagates normal to the surface of the target material. Thus, the tedious alignment issues present with traditional ballistic testing may be avoided. Moreover, the laser pulse parameters for each test shot are readily measured and recorded. In addition, the intensity of the laser pulse may be varied easily and reproduced reliably, enabling easier comparison target materials.

The potential uses for laser shock spallation are many. For example, laser shock spallation may be useful for testing ceramic and glass armor tiles for military body armor and military vehicles, as described herein. The methods may also be useful for testing body armor used by police and armor used in armored cares, bomb squads, and non-military uses of protective armor systems. The methods may also be useful for testing other materials, such as composites used for armor applications and for testing of space and aerospace structures for effects of high velocity impacts. The methods may also be useful for testing adhesion or integrity of various coatings.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" or "having" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A method of evaluating impact resistance of a ceramic material, comprising:
    applying an energy absorbing overlay to a portion of a front surface of the ceramic material;
    applying a substantially transparent overlay upon the energy absorbing overlay;
    directing a pulse of coherent energy to the energy absorbing overlay, generating at least one shockwave for transmission to the ceramic material; and
    detecting spallation on a back surface of the ceramic material.

2. The method of claim 1, the detecting comprising detecting visually.

3. The method of claim 1, further comprising detecting damage within the ceramic material.

4. The method of claim 3, the detecting damage comprising detecting damage ultrasonically.

5. The method of claim 1, further comprising measuring at least one of a diameter and a depth of the spallation.

6. The method of claim 5, further comprising correlating at least one of the diameter and depth of the spallation to at least one laser pulse parameter.

7. The method of claim 6, wherein the laser pulse parameter is selected from at least one of a laser spot diameter, a laser beam energy, a temporal pulse duration, and a laser fluence.

8. The method of claim 1, wherein the ceramic material is selected from silicon carbide, boron carbide, alumina, zirconia, and mixtures thereof.

9. A method of evaluating impact resistance of a glass material, comprising:
    applying an energy absorbing overlay to a portion of a front surface of the glass material;
    applying a substantially transparent overlay upon the energy absorbing overlay;
    directing a pulse of coherent energy to the energy absorbing overlay, generating at least one shockwave for transmission to the glass material; and
    detecting damage within the glass material.

10. The method of claim 9, the detecting comprising at least one of detecting visually and ultrasonically.

11. The method of claim 9, further comprising measuring at least one of a diameter and a depth of the damage.

12. The method of claim 11, further comprising correlating at least one of the diameter and depth of the damage to at least one laser pulse parameter.

13. The method of claim 9, wherein the glass material is selected from borosilicate glass and soda lime glass.

14. A system for evaluating impact resistance of an article, comprising:
    a laser source configured to expose a front surface of the article to a laser beam capable of imparting a shockwave to the article;
    an applicator configured to apply a substantially opaque overlay to the front surface;
    an applicator configured to apply a substantially transparent overlay upon the substantially opaque overlay;
    a detector configured to detect damage in at least one of a back surface of the article and within the article.

15. The system of claim 14, wherein the detector is an ultrasonic detector.

16. The system of claim 14, wherein the article is selected from a ceramic tile and a glass tile.

17. The method of claim 14, wherein the laser pulse parameter is selected from at least one of a laser spot diameter, a laser beam energy, a temporal pulse duration, and a laser fluence.

18. A method for evaluating impact resistance of a material, comprising:
    directing a pulse of coherent energy to a surface of the material, generating at least one shockwave for transmission to the material;
    detecting spallation on an opposite surface of the material; and
    measuring at least one of a diameter and a depth of the spallation.

19. The method of claim 18, further comprising applying at least one of an energy absorbing overlay and a substantially transparent overlay to a portion of the surface of the material to which the pulse of coherent energy is directed.

20. The method of claim 18, further comprising correlating at least one of the diameter and depth of the spallation to at least one laser pulse parameter.

21. The method of claim 20, wherein the laser pulse parameter is selected from at least one of a laser spot diameter, a laser beam energy, a temporal pulse duration, and a laser fluence.

22. The method of claim 18, wherein the material is selected from ceramic material and glass material.

* * * * *